United States Patent [19]

Baur et al.

[11] Patent Number: 5,600,003
[45] Date of Patent: Feb. 4, 1997

[54] PROCESS FOR ISOLATING TETRAPHENYLBORATES

[75] Inventors: Rüdiger Baur, Eppstein; Hermann Fuchs, Königstein; Hans-Tobias Macholdt, Darmstadt, all of Germany; Jörg Gitzel, Tokyo, Japan; Wilfried Theisse, Flörsheim, Germany

[73] Assignee: Hoechst Aktiengesellschaft, Germany

[21] Appl. No.: 370,804

[22] Filed: Jan. 10, 1995

[30] Foreign Application Priority Data

Jan. 11, 1994 [DE] Germany .......................... 44 00 543.1

[51] Int. Cl.$^6$ ....................................................... C07C 5/02
[52] U.S. Cl. .................................................................. 568/1
[58] Field of Search ..................................... 568/1

[56] References Cited

U.S. PATENT DOCUMENTS

| | | |
|---|---|---|
| 3,726,968 | 4/1973 | Loomans . |
| 4,510,327 | 4/1985 | Peet et al. . |
| 4,613,373 | 9/1986 | Umeno et al. . |
| 4,790,960 | 12/1988 | Heckmann et al. . |
| 5,069,821 | 12/1991 | Birmingham et al. . |
| 5,078,974 | 1/1992 | Ashby et al. ............................ 422/187 |
| 5,124,235 | 6/1992 | Fukui et al. . |
| 5,189,222 | 2/1993 | Ashbey et al. ............................... 568/1 |

FOREIGN PATENT DOCUMENTS

| | | |
|---|---|---|
| 0115040 | 6/1965 | Czech Rep. . |
| 0153885 | 9/1985 | European Pat. Off. . |
| 0189799 | 8/1986 | European Pat. Off. . |
| 0353030 | 1/1990 | European Pat. Off. . |
| 0490385 | 6/1992 | European Pat. Off. . |
| 1414256 | 9/1965 | France . |
| 2729193 | 1/1979 | Germany . |

OTHER PUBLICATIONS

Williams, J. L. R., et al, *J. Am Chem. Soc.* 89:5153–5157 (1967).

Gmelin's *Handbuch der Anorganischen Chemie* 33/8, Berlin, Springer–Verlag, 1976, pp. 173–201.

E. Muller, *Houben–Weyl*, "Methoden der Organischen Chemie," vol. 13/3b, Stuttgart, Germany, Georg Thieme Verlag, 1983, pp. 761–797.

Nishida, et al, *Bull. Chem. Soc. Jpn.* 57:2600–2604 (1984).

*Primary Examiner*—Paul J. Killos
*Attorney, Agent, or Firm*—Connolly & Hutz

[57] ABSTRACT

Tetraphenylborates are obtained in an industrially advantageous grade by spray drying an organic, aqueous or organic-aqueous extract of the tetraphenylborate obtainable in the tetraphenylborate synthesis. It is advantageous to treat the specified extract prior to spray drying with pH-controlling auxiliaries and adsorbents to remove byproducts or to limit their formation. The process gives tetraphenylborates in a homogeneous technical grade, i.e. in a narrow particle size distribution and in a particular particle shape, which improves the dispersibility in the medium to be used.

19 Claims, No Drawings

PROCESS FOR ISOLATING TETRAPHENYLBORATES

The present invention relates to an improved process for isolating salt-like tetraphenylborate solids in an industrial grade.

Tetraphenylborates, in particular in the form of their alkali metal salts, are increasingly gaining industrial importance. They are known to be used in the health and cosmetics industry as antitranspirant (U.S. Pat. No. 3,726,968), as antiseptic fungicide in dirt-repelling paints (U.S. Pat. No. 4,613,373), as decontaminating agent for radioactive wastes (U.S. Pat No. 4,790,960), as anionic component for cationic polymers in the field of non-linear optics (EP-A2-0 490 385) and also as polymerization initiator (U.S. Pat. No. 5,124,235).

The synthesis of the tetraphenylborate base has been described many times in the literature. A general overview of possible synthesis processes is given in Gmelin, Handbuch der Anorganischen Chemie, Volume 33/8, p. 173 ff. and Houben-Weyl, Methoden der Organischen Chemie, 4th edition, Volume 13/3b, p. 761 ff. The most frequently used synthetic method is a Grignard reaction of phenylmagnesium chloride with suitable boron components (CS-A-115 040 and U.S. Pat. No. 4,510,327).

A disadvantage of tetraphenylborates is the high market price which is caused by the complicated synthesis, workup and purification and by the instability of tetraphenylborates, particularly in solution. Causes of the instability can be light, acids, strong alkalis and oxidizing agents and also, in particular, the effect of heat in solution. Particularly during the hydrolytic work-up, the tetraphenylborates are present in dissolved form, so that competing decomposition reactions can occur (Nishida, H., et al. Bull. Chem. Soc. Jpn., 57, 2600–2604; Williams, J. L. R. et al., J. Am. Chem. Soc. 89 (1967) 5153). Subsequent stabilization of redissolved tetraphenylborates is possible by means of addition of NaOH or LiOH in aqueous solutions (U.S. Pat. No. 5,069,821).

The significant byproducts of tetraphenylborate production, such as biphenyl, boric acid, triphenylborane and phenol/benzene are formed predominantly during the synthesis and work-up and demand complicated purification steps. The main decomposition product is benzene. The tetraphenylborate can thus be subsequently extracted from the aqueous hydrolysis solution by means of organic solvents such as toluene (U.S. Pat. No. 4,510,327) or benzene (CS-A-115 040).

A disadvantage of the preparative processes used hitherto is that, from today's point of view, ecologically and toxicologically problematical solvents such as, in particular, benzene, toluene and $CHCl_3$ are used and additional organic solvents besides those which have to be present because of the synthesis are used. This means increased expense for disposal or recycling of solvent and increased energy consumption, and a reduction in the space-time yield resulting in increased costs.

It is therefore an object of the present invention to develop a new work-up and isolation process for tetraphenylborates in solid form, which process has an improved space-time yield and in which the use of organic solvents is to be minimized and their reuse is to be sought. Furthermore, the byproduct formation and the decomposition particularly during the hydrolytic work-up and isolation are to be reduced, so as to avoid complicated purification steps. In addition, the work-up and isolation are to be inexpensive and to have as their purpose a tetraphenylborate end product as storage-stable solid in industrially usable quality.

It has now surprisingly been found that the desired tetraphenylborates can be isolated in undecomposed form and in a defined industrial grade as a free-flowing solid by spray drying an organic or aqueous or organic-aqueous tetraphenylborate extract.

The present invention provides a process for isolating tetraphenylborates in solid form, which comprises spray drying an organic or aqueous or organic-aqueous solution or suspension of the tetraphenylborate.

For the purposes of the present invention, generally usable starting materials for spray drying are solutions or suspensions of a tetraphenylborate in aqueous, organic and aqueous-organic mixtures. Suitable solutions and suspensions are those which are obtainable directly from the tetraphenylborate synthesis and also those from which tetraphenylborate is to be recovered.

Suitable spray-drying apparatuses are, for example, cocurrent driers having centrifugal atomization, air sweepers, countercurrent/cocurrent driers having two-fluid nozzle atomization and also two-point discharge of the dry product, countercurrent/cocurrent driers having pressure-nozzle atomization and two-point discharge and also devices based on cocurrent drying and two-nozzle atomization.

Key parameters for the drying of industrial tetraphenylborate solutions or suspensions are primarily the air inlet temperature and the air outlet temperature, which are responsible for the thermal stressing of the product. Other important parameters are the atomizer characteristics and the amount of carrier gas which, together with the coupled temperature (ratio of inlet temperature and outlet temperature), determine the spraying performance. Thus, in the use of atomizer disks, speed and shape, for example the hole diameter, are of importance.

For aqueous tetraphenylborate solutions or suspensions, suitable conditions are, for example, air inlet temperatures advantageously between 100° C. and 400° C., preferably between 180° and 250° C., and air outlet temperatures between 50° C. and 180° C., preferably between 70° and 120° C. For organic tetraphenylborate solutions or suspensions, the inert gas inlet temperatures are advantageously between 150° C. and 200° C. and the inert gas outlet temperatures are between 50° C. and 150° C. When using a cocurrent drier having centrifugal atomization, suitable conditions are atomizer disk speeds between 10,000 and 50,000 rpm and hole sizes between 0.5 mm and 5 mm.

The concentration of the tetraphenylborate in the solution or suspension to be spray dried is advantageously from 1 to 40% by weight, preferably from 1 to 25% by weight, regardless of whether an aqueous, organic or aqueous-organic extract is used. For aqueous extracts, a concentration of from 1 to 15% by weight is particularly preferred.

Surprisingly, despite the high temperatures occurring during spray drying, tetraphenylborates are obtained in a particularly homogeneous industrial quality which is described in more detail below.

In a preferred embodiment of the process of the invention, the tetraphenylborate is prepared by a conventional Grignard reaction and the resulting Grignard reaction solution is worked up by a combination of the process steps a) to d):

a) hydrolysis of the Grignard reaction solution in the presence of a pH-controlling auxiliary, b) adsorptive purification of the hydrolysis solution, c) solvent replacement of the organic solvents with water and d) spray drying of the aqueous extract from c).

The starting material is an ether-containing Grignard reaction solution obtainable by methods known in the literature from the reaction of a boric ester with a phenylmagnesium halide. Boric esters which are of interest are, for example: methyl borate, propyl borate, butyl borate and amyl borate (Gmelin, Handbuch der Anorganischen Chemie, Volume 33/8, p. 173 ff; Holzapfel, H. and Richter, C., J. Prakt. Chem. 26 (1964) 5–23).

a) The hydrolysis of the said Grignard reaction solution is carried out with addition of pH-controlling auxiliaries. Suitable pH-controlling auxiliaries are organic or inorganic bases, preferably an alkali metal salt of acetic acid, lactic acid or tartaric acid, an alkali metal hydroxide, alkaline earth metal hydroxide, an alkali metal carbonate, an alkaline earth metal carbonate, an alkali or alkaline earth metal salt of a phosphate or hydrogen phosphate or a mixture of at least two of the materials specified, in particular sodium hydrogen phosphate, sodium carbonate, sodium acetate, sodium lactate and magnesiumhydroxide. Further compounds of interest are sulfides, silicates, amines, phthalates, citrates, oxalates, preferably their alkali metal or alkaline earth metal salts. Preference is given to mixtures of from 2 to 5, preferably 2 or 3, different pH-controlling auxiliaries.

The hydrolysis is carried out by initially charging an aqueous or aqueous-organic solution or suspension of the pH-controlling auxiliaries and metering in the Grignard reaction solution over a period of from 5 to 60 minutes, preferably from 5 to 30 minutes, if desired by means of applied pressure, e.g. using $N_2$, while stirring, preferably at from 5 to 50 rpm. The concentration of the specified auxiliaries is between 0.1 and 50% by weight, preferably between 0.5 and 15% by weight, in particular between 1 and 10% by weight, based on the weight of the hydrolysis product from the Grignard reaction solution. The pH-controlling auxiliaries establish a pH$\geq$7, preferably from 7 to 11, in particular from 7.5 to 10.5, in the aqueous or aqueous-organic hydrolysis solution. The starting temperature of the Grignard solution to be hydrolyzed is from $-20°$ to $+60°$ C., preferably from 0° to 50° C., in particular from 5° to 40° C. Metering in is followed by stirring for a further period of preferably from 5 to 120 minutes at a temperature between 0° and 60° C. It is advantageous to add an additional amount of the alcohol of the boric ester component or the ether of the Grignard reaction solution to the hydrolysis mixture after hydrolysis and to stir further. The added weight of alcohol or ether is advantageously from 0.5 to 5 times, preferably from 1 to 3 times, the amount of ether in the Grignard reaction solution.

Table 1 below gives the change in the pH and the proportion of certain byproducts, with and without an addition of pH-controlling auxiliaries, during the hydrolysis step. Unless otherwise indicated, the percentages are relative values obtained by HPLC analysis (% by area, 100% is the sum of all substances detected). The hydrolysis temperature is from 25° to 35° C., without addition of adsorbents. "Tri" is triphenylborane.

TABLE 1

| Additives in % by weight | Byproducts | | | pH values | | |
| --- | --- | --- | --- | --- | --- | --- |
| | tri | benzene | biphenyl | pH$_{Start}$ | pH$_{5 sec}$ | pH$_{END}$ |
| Without additives | 2.0% | 1.0% | 33% | 6.8 | 9.6 | 8.8 |
| 5% Na$_3$PO$_4$ × 10 H$_2$O | 2.0% | 1.0% | 32% | 11.9 | 11.7 | 8.8 |
| 5% Mg (OH)$_2$ | 4.2% | 0.4% | 0.4% | 10.1 | 10.2 | 8.9 |
| 20% Mg (OH)$_2$ | 1.8% | 0% | 0.2% | 9.6 | 9.8 | 8.5 |
| 5% Sodium lactate | 10.1% | 0.4% | 0.7% | 6.7 | 10.8 | 9.1 |
| 20% Sodium lactate | 23.9% | 0.3% | 1.2% | 6.7 | 10.6 | 10.9 |
| 5% Sodium acetate | 0% | 2.0% | 8% | 8.5 | 10.8 | 8.9 |
| 20% Sodium acetate | 0% | 3.0% | 12% | 9.6 | 10.4 | 8.8 |

The tetraphenylborate percentages have their highest values of 91% and 96% when using a Mg(OH)$_2$ suspension as pH-controlling auxiliary. Without an additive the concentration is 59%. A significant increase in yield is thus achieved by addition of pH-controlling auxiliaries.

The formation of the byproducts tri, benzene and biphenyl resulting from Grignard side reactions and hydrolytic degradation is dependent in a different way on the presence of pH-controlling auxiliaries. Thus, the tri amount in particular is decreased by means of acetate, while the biphenyl amount is decreased by means of Mg(OH)$_2$. For this reason, mixtures of pH-controlling auxiliaries are advantageous.

It is furthermore apparent that certain byproducts are preferentially formed at pH values below pH 7 and above pH 11.

The addition of pH-controlling auxiliaries can also be carried out in solution to avoid decomposition of tetraphenylborates, for example if storage of the solution is necessary for technical process reasons.

b) The adsorptive purification of the hydrolysis solution is carried out by addition of an adsorbent to the hydrolysis solution prior to or after the hydrolysis reaction, but at the latest before the spray drying step d). The adsorbent can be introduced into the hydrolysis solution together with the pH-controlling auxiliaries or be added to the tetraphenylborate solution after hydrolysis is complete; it is here immaterial whether the solution is an aqueous or aqueous-organic mixture. Suitable adsorbents are activated carbon, zeolites such as, for example, ZSM types, offretite, mordenite, ferrierite and erionite types, aluminum oxide, high-surface-area silicon oxides and silicates, and also polymers, adsorber resins such as crosslinked poly(N-vinylimidazole), poly-(N-vinylpyridine) or methylenebisacrylamide-crosslinked poly(N-vinylimidazole), and also mixtures of the specified materials.

The amounts of adsorbents used are between 0.001 and 20% by weight, preferably between 0.01 and 10% by weight, in particular between 0.1 and 10% by weight, based on the total amount of solvent in which the tetraphenylborate active compound is present. The contact time is advantageously from 1 to 45 minutes, preferably from 5 to 30 minutes and particularly preferably from 5 to 20 minutes, with the temperature while stirring being from 0° to 60° C., preferably from 5° to 55° C. and particularly preferably from 10° to 50° C., and the separation from the mixture after adsorption is complete being carried out by filtration, preferably through a bed filter.

Table 2 below shows the effect of an adsorbent, in this case a mixture of an obsidian-like natural material of vulcanic origin (natural glass) consisting essentially of $SiO_2$ (about 75%), $Al_2O_3$ (about 13%), $Na_2O$ (about 5%), $K_2O$ (about 5%) and various metal oxides, for example Perlite J4 (from Lehmann, Voss & Co., Hamburg), and activated carbon, in the absence and in the presence of various salts and/or pH-controlling auxiliaries. Percentages are by weight in the hydrolysis solution in the case of benzene, in the case of biphenyl they are HPLC percentage areas analogous to Table 1. Temperature: 25° C., contact time of the adsorbent: 15 minutes.

TABLE 2

| Additive | Byproduct | |
|---|---|---|
| Perlite/activated carbon and | biphenyl | benzene |
| NaCl | 0.8 | 0.007% by weight |
| NaCl + $Na_2CO_3$ | not detectable | 0.003% by weight |
| — | 0.3% | 0.001% by weight |

Comparison with the values from Table 1 clearly shows that the addition of adsorbents significantly reduces the biphenyl and benzene contents. The adsorptive purification is selective for benzene and biphenyl, while the tri concentration is relatively unaffected.

In contrast, pH-controlling auxiliaries primarily counter the formation of tri and biphenyl, while the effect on the formation of benzene is small (Table 1). A combination of pH-controlling auxiliaries and adsorptive purification is therefore particularly effective.

Preferred process variants of the clarifying filtration are:
Variant 1:
  1 kg of Perlite J4, based on 40 kg of pure tetraphenylborate, are metered at a temperature of 50° C. into an about 10% strength by weight solution of the tetraphenylborate salt. The suspension is stirred for 15 minutes and the adsorbent is subsequently separated off by filtration.
Variant 2:
  250 kg of a 10% strength by weight tetraphenylborate solution are treated with a suspension of 2 kg of activated carbon and Perlite J4 in 65 kg of demineralized water at from 30° to 50° C. The separation of the adsorbent is likewise by filtration.
Variant 3:
  50 ml of an about 10% strength by weight tetraphenylborate solution are admixed with a mixture of 0.6 g of $Al_2O_3$ (neutral or alkaline), 0.3 g of Perlite J4 and 0.3 g of activated carbon and stirred for a total of 45 minutes at 15° C., with the solution being first stirred for 15 minutes with $Al_2O_3$, activated carbon/Perlite being subsequently added and the mixture being stirred for a further 30 minutes.

Basic or neutral $Al_2O_3$ has been found to be particularly suitable, since when this is used neither benzene nor biphenyl were detected.

c) After hydrolysis of the Grignard reaction solution, solvent replacement of the organic solvents by water is carried out, preferably by distillative removal of the organic solvents and addition of water prior to distillation. It is advantageous to carry out the distillation at a temperature below 70° C., preferably between 20° and 50° C. If required, the distillation can be carried out under reduced pressure, for example between 50 and 500 mbar. It is advantageous for the aqueous and organic phases prior to distillation to have approximately equal volumes. Furthermore, it is advantageous if the aqueous phase contains the abovementioned pH-controlling auxiliaries in the concentrations specified for the hydrolysis reaction. If desired, a further addition of a pH-controlling auxiliary to the aqueous phase is made prior to distillation.

After distillation, the concentration of the desired active compound in the aqueous phase is, depending on temperature, from 1 to 25% by weight, preferably from 5 to 20% by weight, in particular from 5 to 15% by weight.

d) The aqueous phase remaining as residue after distillation, which contains the active compound in the abovementioned concentrations in solution or in suspension, is subsequently spray dried as described above.

Tetraphenylborate is preferably isolated in solid form in the form of a salt readily soluble in water, in particular as a sodium, lithium, magnesium or magnesium chloride salt, or as a mixture of a plurality of these salts, with the cations present naturally being predominantly those which were present or added in excess in the respective solution during the preparation of tetraphenylborate, for example by a Grignard reaction, and during the hydrolysis. If lithium tetraphenylborate is to be prepared, appropriate amounts of a lithium salt have to be added.

It is known that tetraphenylborates are temperature sensitive, particularly in solution. It has been found that temperatures above 80° C. effect significant decomposition of the tetraphenylborate, even at a residence time of 30 minutes. Table 3 below shows the amount of sodium tetraphenylborate still present in percentages relative to the amount used (100%) as a function of temperature. The residence time at the given temperature is in each case 30 minutes:

TABLE 3

| Amount/active compound in % | Temperature |
|---|---|
| 100 | 70° C. |
| 90 | 80° C. |
| 80 | 85° C. |
| 50 | 90° C. |
| 10 | 95° C. |

Above 90° C., the decomposition progresses quickly. It was therefore particularly surprising that tetraphenylborates survive short-term but high temperature stresses >90° C., as occur, for example, during spray drying, without significant decomposition.

The active compound obtainable from spray drying corresponds to the desired technical grade, as described below. The solid tetraphenylborates prepared by the process of the invention have the following product properties:

Residual moisture (dissolved and determined by the Karl-Fischer method). Between 0.001 and 8% by weight, preferably between 0.01 and 6% by weight, in particular between 0.05 and 5% by weight, of water.

The conductivity of a 10% strength by weight aqueous solution is from 10 to 20 mS/cm.

The intrinsic pH in a 10% strength by weight aqueous solution is from pH 7.0 to 11, preferably from pH 8 to 10.5.

Differential thermal analysis (DTA): the thermal stability of the technical-grade solid is shown by no decomposition occurring up to 400° C. at a heating rate of 3 K/min.

The dielectric parameters (DP) of the technical-grade tetraphenylborate solid have the following values:
  the specific resistance determined on a pretreated pressed disk (diameter 4 cm) having a thickness of from 0.8 to 1.6 mm is from $1 \times 10^9 \Omega \cdot cm$ to $9 \times 10^{16} \Omega \cdot cm$, preferably from $1 \times 10^9$ to $9 \times 10^{15} \Omega \cdot cm$.

the dielectric loss factor tan δ determined as a function of frequency on the same test specimen is between $5 \times 10^{-1}$ and $1 \times 10^{-3}$, determined at 1 kHz between $9 \times 10^{-1}$ and $5 \times 10^{-3}$.

the dielectric constant ε, determined at 1 kHz, is from 3 to 11.

The crystallinity of the technical-grade solid, characterized by an X-ray diffraction pattern, shows a crystalline content of >50%, particularly preferably between 60% and 100%, with the 2 theta measuring region showing two particularly intense reflections of which the first is between 6 and 15 (2 theta) and the second is between 18 and 24 (2 theta).

A particular feature which distinguishes a solid tetraphenylborate prepared according to the invention from a tetraphenylborate of the prior art is the particle shape and the particle size and their distribution widths. While a tetraphenylborate corresponding to the prior art comprises primarily cuboid-, rod- or needle-shaped crystallites, the particles of a tetraphenylborate of the invention have a round, oval or at least a rounded shape, preferably a spherical shape, with the particles being able to have crater-like depressions.

Table 4 below shows a comparison of the particle size distribution of three samples of commercially available sodium tetraphenylborate corresponding to the prior art (samples 1, 2, 3) with two samples (samples I and II) of the tetraphenylborate of the invention in the form of its sodium salt.

TABLE 4

| % by weight $d_x$ values | Sample I | Sample II | Sample 1 | Sample 2 | Sample 3 |
|---|---|---|---|---|---|
| | | | Particle size in [μm] | | |
| $d_{10}$ | 3 | 1 | 15 | 5 | 16 |
| $d_{50}$ | 13 | 16 | 98 | 38 | 92 |
| $d_{95}$ | 29 | 42 | 350 | 320 | 360 |
| Δ ($d_{95}-d_{10}$) | 26 | 41 | 335 | 315 | 344 |

Table 4 demonstrates that the samples according to the invention are not only significantly finer ($d_{50}$ and $d_{95}$ values), but also have a significantly narrower particle size distribution $\Delta(d_{95}-d_{10})$ and thus show greater homogeneity. The particle size can be defined by the $d_{95}$ value or the $d_{50}$ value. The d95 value is between 0.1 μm and 250 μm, preferably between 0.5 μm and 150 μm, the $d_{50}$ value is between 0.1 μm and 30 μm, preferably between 1 μm and 25 μm.

The particle size distribution Δd is defined by the difference $d_{95}-d_{10}$ and is between 5 and 150 μm, preferably between 10 and 100 μm.

The particle size, particle shape and narrow particle size distribution of the tetraphenylborates of the invention give a number of advantages in use, for example improved dispersibility in resin, wax or paste-like media and a higher bulk density.

The present invention also provides a compound of the formula (I) in solid form

(I), where $X^\oplus$ is $Na^\oplus$, $Li^\oplus$, $Mg^{2+}/2$ or $MgCl^+$, wherein the particle shape of the solid particles is predominantly spherical, round or oval.

EXAMPLE 1

79.0 g of $Mg(OH)_2$ are homogeneously suspended in 316.0 g of demineralized water and homogeneously mixed with a solution of 65.3 g of NaCl in 400 g of deionized water. The initial pH is 9.9. This aqueous suspension is metered over a period of 3.5 minutes into a Grignard solution containing 0.41 mol of phenylmagnesium chloride as Grignard reagent and 0.103 mol of a boric ester. The final temperature is 39° C., the final pH 8.5.

After 15 minutes, the pH is constant (9.1) and the temperature is 29° C. For the extraction, 100 g of the alcohol corresponding to the alcohol component of the boric ester are added, stirred for a further 30 minutes at 25° C. and separated off via a separation vessel. The alcoholic extract is admixed with 150 g of $H_2O$ and freed by distillation of the alcohol and of the ether of the Grignard solution, with the liquid phase temperature not exceeding 70° C. The alcohol distilled off can be recovered and used again for extraction. For the purification, 2% by weight of activated carbon and 2% by weight of a kieselguhr, for example ®Celite, are subsequently added, stirred for 15 minutes at 22° C., filtered off and the filtrate is transferred to a spray drier. Spray drying is carried out at an air inlet temperature of 220° C. and an outlet temperature of 80° C.

The resulting powder product has the following properties:

| 1. DTA: | decomp. >400° C. |
|---|---|
| 2. Crystallinity: | >60% |
| 3. DP | |
| a) resistance: | $1 \times 10^9$ (Ω · cm) |
| b) tan δ: | $5 \times 10^{-1}$ (1 kHz) |
| c) ε: | 10 (1 kHz) |
| 4. Intrinsic pH: | 9.3 |
| 5. Conductivity: | 14.1 mS/cm |
| 6. Particle size distribution: | $d_{95} = 29$ μm, Δ 26 μm |
| 7. Residual moisture: | 0.2% |

EXAMPLE 2

20 g of $Mg(OH)_2$ are suspended in 316.0 g of demineralized water and mixed at 25° C. with 8 g of sodium acetate and 65.3 g of NaCl dissolved in 400 g of deionized water. Over a period of 3.5 minutes, this aqueous mixture is, with the aid of pressure, metered into a Grignard reaction solution containing 0.41 mol of phenylmagnesium chloride as Grignard reagent and 0.103 mol of a boric ester. The final temperature is 40° C., the final pH is 8.5. After 15 minutes, the pH is constant (9.1) and the temperature is about 30° C.

For the extraction, 100 g of the alcohol corresponding to the alcohol component of the boric ester are added, the mixture is intensively stirred for a further 30 minutes at 25° C. and separated via a separation vessel.

The alcoholic extract is admixed with 150 g of demineralized water and freed by distillation of alcohol, with the liquid-phase temperature being between 30° and 65° C., depending on the vacuum used.

The alcohol distilled off is recycled and can be used again for the extraction in the next batch. For the purification, 1% by weight each of activated carbon and Celite are subsequently added and the mixture is stirred for 15 minutes. at 20° C.

The solid is subsequently filtered off and the aqueous 10% strength by weight solution is spray dried in a spray drier.

Spray drying is carried out at an air inlet temperature of 220° C. and an outlet temperature of 90° C.

The resulting powder product has the following properties:

| 1) DTA: | decomp. > 400° C. |
|---|---|
| 2) Crystallinity: | >60% |
| 3) DP | |
| a) resistance: | $3 \times 10^9$ ($\Omega \cdot$ cm) |
| b) tan $\delta$: | $3 \times 10^{-1}$ (1 kHz) |
| c) $\epsilon$: | 8 (1 kHz) |
| 4) Intrinsic pH, 10% strength solution: | 9.4 |
| 5) Conductivity, 10% strength solution: | 15.3 mS/cm |
| 6) Particle size distribution: | $d_{95}$ = 29 µm, $\Delta$ = 26 µm |
| 7) Residual moisture: | 0.2% |

EXAMPLE 3

500 kg of water to which 100 kg of calcined $Na_2CO_3$ have been added as a pH-stabilizing auxiliary are heated to from 40° to 45° C. in a steel reactor having a volume of 1.2 m³ and fitted with frame stirrer, 30 l glass feed vessel, tube for vapors, glass condenser and thermometer. 285 l of Grignard reaction solution are metered into the hydrolysis solution over a period of 10 minutes. It is also advantageous for the metered addition to be carried out by means of applied protective gas pressure ($N_2$/Ar). During the metered addition, the reaction solution is intensively stirred.

After the metered addition, a temperature of from 45° to 55° C. is established and the mixture is stirred for a further 45 minutes. After cooling to from 10° to 25° C., the organic upper phase is separated from the two-phase mixture formed, 150 kg of an alcohol corresponding to the alcohol component of the boric ester or of an ether corresponding to the ether used for the preparation of the Grignard reagent are metered in, the mixture again intensively stirred for 30 minutes and phase separation is carried out.

250 kg of water are added to the combined organic phases and the organic phase is distilled off at a pressure of between 50 and 500m bar at temperatures below 70° C. After distillation, 2 kg of activated carbon and 2 kg of Perlite J4 are added, the mixture stirred briefly at from 25° to 50° C. and the solid filtered off through a single-bed filter.

The filtrate is spray dried at an air inlet temperature of from 210° to 230° C. and an air outlet temperature of from 80° to 100° C.

The resulting powder product has the following quality:

| 1) DTA | decomp. >400° C. |
|---|---|
| 2) Crystallinity: | >60% |
| 3) DP | |
| a) resistance: | $1.3 \times 10^{13}$ $\Omega \cdot$ cm |
| b) dielectric loss factor: | $3 \times 10^{-2}$ (1 kHz) |
| c) dielectric constant $\epsilon$: | 4.8 (1 kHz) |
| 4) Intrinsic pH (25° C.), 10% strength solution: | 9.4 |
| 5) Conductivity, 10% strength solution: | 3.5 mS/cm |
| 6) Particle size: | $d_{95}$ = 43 µm, $\Delta$ = 41 µm |
| 7) Residual moisture: | 0.33% |

The suitability of the technical quality is demonstrated by the reaction to give tetrabutylammonium tetraphenylborate. The product gives:

| a) Intrinsic pH: | 7.3 |
|---|---|
| b) Conductivity: | 19.5 µS/cm |
| c) Thermal stability (mp.): | 234° C. |

We claim:

1. A process for the isolation of a tetraphenylborate, in solid form, from a solution or suspension containing 1 to 40% by weight of a tetraphenylborate and water, an organic solvent, or a mixture thereof as the solution or suspension medium, which process comprises:

spray drying a said solution or suspension by atomizing the solution or suspension and heating the resulting atomized solution or suspension in a spray drying zone with a heated gas which enters the spray drying zone at a temperature in the range of 100° to 400° C. and exits the spray drying zone at a temperature in the range of 50° to 180° C., and recovering as the product a solid, particulate tetraphenylborate having a residual moisture content between 0.001 and 8% by weight.

2. The process as claimed in claim 1, wherein the tetraphenylborate is prepared by a Grignard reaction and the work up of the Grignard reaction solution is a combination of the process steps a) to d):

a) hydrolysis of the Grignard reaction solution in the presence of a pH-controlling auxiliary, b) adsorptive purification of the hydrolysis solution, c) solvent replacement of the organic solvents with water and d) spray drying of the aqueous extract from c).

3. The process as claimed in claim 2, wherein the adsorptive purification is carried out by addition of an adsorbent to the hydrolysis solution prior to or after hydrolysis, but prior to spray drying.

4. The process as claimed in claim 2, wherein an adsorbent is added to the aqueous phase after the solvent replacement.

5. The process as claimed in claim 2, wherein the adsorptive purification is carried out by addition of activated carbon, zeolites, aluminum oxide, high-surface-area silicon oxides, silicates or a mixture of said adsorbents.

6. The process as claimed in claim 2, wherein the solvent replacement c) is followed by a further addition of a pH-controlling auxiliary.

7. The process as claimed in claim 2, wherein the pH-controlling auxiliary is an organic or inorganic base.

8. The process as claimed in claim 7, wherein the pH-controlling auxiliary is an alkali metal salt of acetic acid, lactic acid or tartaric acid, an alkali metal hydroxide, an alkaline earth metal hydroxide, an alkali metal carbonate, an alkaline earth metal carbonate, an alkali metal or alkaline earth metal salt of a phosphate or hydrogen phosphate or a mixture of at least two of said materials.

9. The process as claimed in claim 2, wherein the pH-controlling auxiliary is present in a concentration of from 0.1 to 50% by weight, based on the weight of the hydrolysis product from the Grignard reaction solution, so that the pH of the hydrolysis solution is between pH 7 and 11.

10. The process as claimed in claim 9, wherein the pH-controlling auxiliary is present in a concentration of from 0.5 to 15% by weight, based on the weight of the hydrolysis product from the Grignard reaction solution, so that the pH of the hydrolysis solution is between pH 7.5 and 10.5.

11. The process as claimed in claim 9, wherein the pH-controlling auxiliary is present in a concentration of from 1 to 10% by weight, based on the weight of the hydrolysis product from the Grignard reaction solution, so that the pH of the hydrolysis solution is between pH 7.5 and 10.5.

12. The process as claimed in claim 2, wherein the solvent replacement is carried out by distillative removal of the solvent after addition of water.

13. The process as claimed in claim 12, wherein the distillative removal of the solvent is carried out under reduced pressure and at temperatures below 70° C.

14. The process as claimed in claim 13, wherein the distillative removal of the solvent is carried out under reduced pressure and at temperatures between 20° and 50° C.

15. The process as claimed in claim 1, wherein the concentration of the tetraphenylborate in the solution or suspension to be spray dried is from 1 to 25% by weight.

16. The process as claimed in claim 1, wherein the tetraphenylborate is isolated in the form of a water-soluble salt.

17. The process as claimed in claim 16, wherein the tetraphenylborate is isolated as a lithium, sodium, magnesium or magnesium chloride salt or a mixture of said salts.

18. The process as claimed in claim 1, wherein said solution or suspension comprises an aqueous solution, and wherein said heated gas is air.

19. The process as claimed in claim 1, wherein said solution or suspension contains an organic solvent; said heated gas is an inert gas heated to 150° to 200° C.; and the heated gas exits the spray drying zone at a temperature in the range of 50° to 150° C.

* * * * *